US012319696B2

(12) United States Patent
Westman

(10) Patent No.: US 12,319,696 B2
(45) Date of Patent: Jun. 3, 2025

(54) 2,6-DIMETHYL-N-((PYRIDIN-4-YL)METHYL)IMIDAZO[1,2-B]PYRIDAZIN-8-AMINE AND 2,5-DIMETHYL-N-[(PYRIDIN-4-YL)METHYL]PYRAZOLO[1,5-A]PYRIMIDIN-7-AMINE DERIVATIVES FOR TREATING VIRAL INFECTIONS

(71) Applicant: CUROVIR AB, Kalmar (SE)

(72) Inventor: Jacob Westman, Järlåsa (SE)

(73) Assignee: CUROVIR AB, Kalmar (SE)

( * ) Notice: Subject to any disclaimer, the term of this patent is extended or adjusted under 35 U.S.C. 154(b) by 1011 days.

(21) Appl. No.: 17/282,064

(22) PCT Filed: Aug. 20, 2019

(86) PCT No.: PCT/EP2019/072220
§ 371 (c)(1),
(2) Date: Apr. 1, 2021

(87) PCT Pub. No.: WO2020/074159
PCT Pub. Date: Apr. 16, 2020

(65) Prior Publication Data
US 2021/0340147 A1    Nov. 4, 2021

(30) Foreign Application Priority Data
Oct. 10, 2018  (EP) ..................... 18199486

(51) Int. Cl.
*C07D 487/04* (2006.01)
*A61K 9/127* (2025.01)

(52) U.S. Cl.
CPC ............ *C07D 487/04* (2013.01); *A61K 9/127* (2013.01)

(58) Field of Classification Search
CPC .... C07D 487/04; A61K 9/127; A61K 31/519; Y02A 50/30; A61P 31/12; A61P 31/14; A61P 31/16
See application file for complete search history.

(56) References Cited

U.S. PATENT DOCUMENTS 6,313,124 B1    11/2001   He et al.
9,963,455 B2 *   5/2018   Westman ............ A61K 31/519

FOREIGN PATENT DOCUMENTS

| WO | 2010086040 A1 | 8/2010 |
| WO | 2013128029 A1 | 9/2013 |
| WO | 2015110491 A2 | 7/2015 |
| WO | 2016206999 A1 | 12/2016 |
| WO | 2018185120 A1 | 10/2018 |

OTHER PUBLICATIONS

Patani, G. A. et al. "Bioisosterism: A Rational Approach in Drug Design." Chemical reviews, 1996. vol. 96, 8: 3147-3176. (Year: 1996).*
Wu, Y. J. et al. Fluorine substitution can block CYP3A4 metabolism-dependent inhibition: identification of (S)—N-[1-(4-fluoro-3-morpholin-4-ylphenyl)ethyl]-3-(4-fluorophenyl)acrylamide as an orally bioavailable KCNQ2 opener devoid of CYP3A4 MDI. J Med Chem, 2003. vol. 46(18): 3778-3781. (Year: 2003).*
Barlow, et al., "Autophagy in Diabetes:?—Cell Dysfunction, Insulin Resistance, and Complications," DNA And Cell. Biol, 2015, 34(4), 252-260).
Bianco et al., "Metabolism of Phosphatidylinositol 4-Kinase IIIα-Dependent PI4P is Subverted by HCV and is Targeted by a 4-Anilino Quinazoline with Antiviral Activity," PLoS Pathogens, 2012, 8(3), 1-17).
Catalano et al., "Phenoxide leaving group SNAr strategy for the facile preparation of 7-amino-3-aryl pyrazolo[1,5-a]pyrimidines from a 3-bromo-7-phenoxypyrazolo[1,5-a]pyrimidine intermediate," Tetrahedron Lett. 2015, 56, 6077-6079.
Chen et al. , "Optimization of 3-phenylpyrazolo[1,5-a]pyrimidines as potent corticotropin-releasing factor-1 antagonists with adequate lipophilicity and water solubility," Bioorg. Med. Chem. Lett. 2004, 14, 3669-3673.
Décor et al., "Design, synthesis and biological evaluation of novel aminothiazoles as antiviral compounds acting against human rhinovirus," Bioorg. Med. Chem. Letters 23 2013, 3841-3847.
Gilligan et al., "8-(4-Methoxyphenyl) pyrazolo[1,5-a]-1,3,5-triazines: Selective and Centrally Active Corticotropin-Releasing Factor Receptor-1 (CRF1) Antagonists," J. Med. Chem. 2009, 52, 3073-3083.

(Continued)

*Primary Examiner* — Jean P Cornet
*Assistant Examiner* — Chihyi Lee
(74) *Attorney, Agent, or Firm* — Renner, Otto, Boisselle & Sklar, LLP

(57) ABSTRACT

A compound of formula (I)

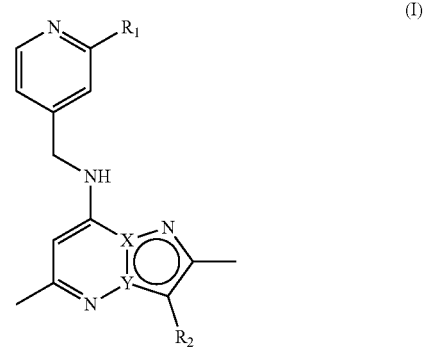

or a pharmaceutically acceptable salt thereof, wherein one of X and Y is O and the other one is N; $R_1$ is selected from halogen, CN, $NH(CH_3)$, $N(CH_3)_2$, C1-C4 alkoxy wherein the alkyl moiety of the C1-C4 alkoxy is optionally substituted by 1-3 halogens, and C1-C4 alkyl, wherein the C1-C4 alkyl is optionally substituted by 1-3 halogens, CN, $NH(CH_3)$, or $N(CH_3)_2$; and $R_2$ is 3,4-dimethoxyphenyl or 1,3-dimethyl-1H-indazol-5-yl.

15 Claims, No Drawings

(56) References Cited

OTHER PUBLICATIONS

Griffith et al., "Discovery and evaluation of pyrazolo[1,5-a]pyrimidines as neuropeptide Y1 receptor antagonists," Bioorg. Med. Chem. Lett. 2011, 21, 2641-2645.

Gudmundsson et al., "Pyrazolopyrimidines and pyrazolotriazines with potent activity against herpesviruses," Bioorg. Med. Chem. Lett. 2009, 19, 5689-5692.

Hwang et al., "Discovery and characterization of a novel 7-aminopyrazolo[1,5-a]pyrimidine analog as a potent hepatitis C virus inhibitor," Bioorg. Med. Chem. Lett. 2012, 22, 7297-7301.

Kusakabe, "Discovery of Imidazo[1,2-b] pyridazine Derivatives: Selective and Orally Available Mps1 (TTK) Kinase Inhibitors Exhibiting Remarkable Antiproliferative Activity," J. Med. Chem. 2015, 58, 1760-1775.

Lai et al., "The Autophagic Machinery in Enterovirus Infection," Viruses, 2016, 8(32), 1-13.

Lamarche et al., "Anti-Hepatitis C Virus Activity and Toxicity of Type III Phosphatidylinositol-4-Kinase Beta Inhibitors," Antimicrobial Agents and Chemotherapy 2012, 56(10), 5149-5156.

Levine et al., "Autophagy in the Pathogenesis of Disease," Cell, 2008, 132(1), 27-42.

Majo et al., "Facile Palladium-Catalyzed Synthesis of 3-Arylpyrazolo-[1,5-a] pyrimidines," Adv. Synth. Catal. 2003, 345, 620-624.

Mcleod et al., "Identification of a Series of Compounds with Potent Antiviral Activity for the Treatment of Enterovirus Infections," ACS Med. Chem. Lett. 2013, 4(7), 585-589.

Mejdrova et al., "Highly Selective Phosphatidylinositol 4-Kinase IIIβ Inhibitors and Structural Insight into Their Mode of Action," (J. Med. Chem., 2015, 58 (9), 3767-3793.

Mejdrova et al., "Rational Design of Novel Highly Potent and Selective Phosphatidylinositol 4-Kinase IIIβ (PI4KB) Inhibitors as Broad-Spectrum Antiviral Agents and Tools for Chemical Biology," J. Med. Chem., 2017, 60 (1), 100-118.

Polajnar et al., "Impaired autophagy: a link between neurodegenerative and neuropsychiatric diseases," J Cell. Mol. Med. 2014, 9(18). 1705-1711.

Sala et al., "Purine analogs as phosphatidylinositol 4-kinase IIIβ inhibitors," Bioorg. Med. Chem. Lett. 2016, 26(11), 2706-2712.

Sridhar et al., "The lipid kinase PI4KIIIβ preserves lysosomal identity," EMBO J. 2013,32, 324-339.

Tellew et al., "Discovery of NBI-77860/GSK561679, a potent corticotropin-releasing factor (CRF1) receptor antagonist with improved pharmacokinetic properties," Bioorg. Med. Chem. Lett. 2010, 20, 7259-7264.

Van Der Schaar et al., "A Novel, Broad-Spectrum Inhibitor of Enterovirus Replication That Targets Host Cell Factor Phosphatidylinositol 4-Kinase IIIβ," Antimicrobial Agents Chemother. 2013, 57(10), 4971-4981.

Wagner et al., "A Selective Cannabinoid-1 Receptor Antagonist, PF-95453, Reduces Body Weight and Body Fat to a Greater Extent than Pair-Fed Controls in Obese Monkeys,"Pharm. Exp. Ther. (2010), 335(1), 103-113.

Yang et al., "Phosphatidylinositol 4-Kinase IIIβ is Required for Severe Acute Respiratory Syndrome Coronavirus Spike-mediated Cell Entry," J. Biol. Chem. 2012, 287(11), 8547-8467.

International Search Report and Written Opinion for corresponding International Application No. PCT/EP2019/072220 dated Oct. 17, 2019.

Labroli et al., "Discovery of pyrazolo[1,5-a]pyrimidine-based CHK1 inhibitors:a template-based approach—Part 2," Bioorg. Med. Chem. Lett. 2011, 21, 471-474.

Guengerich, "Inhibition of Cytochrome P450 Enzymes by Drugs—Molecular Basis and Practical Applications," Biomol. Ther. Sep. 3, 2021, 30(1), 1-18.

* cited by examiner

2,6-DIMETHYL-N-((PYRIDIN-4-YL)METHYL) IMIDAZO[1,2-B]PYRIDAZIN-8-AMINE AND 2,5-DIMETHYL-N-[(PYRIDIN-4-YL)METHYL] PYRAZOLO[1,5-A]PYRIMIDIN-7-AMINE DERIVATIVES FOR TREATING VIRAL INFECTIONS

This application is a national phase of International Application No. PCT/EP2019/072220 filed Aug. 20, 2019 and published in the English language, which claims priority to European Application No. 18199486.4 filed Oct. 10, 2018, the entire disclosures of which are hereby incorporated by reference.

FIELD OF THE INVENTION

The present invention relates generally to compounds having usefulness in therapy, in particular in the treatment of conditions caused by certain viruses, such as common cold, encephalitis, meningitis, myocarditis, conjunctivitis, pancreatitis, as well as diabetes, cancer, and neurodegenerative diseases, such as Alzheimer's disease and amyotrophic lateral sclerosis. More particularly the invention relates to certain aminosubstituted heteroaromatic compounds and their use in therapy.

BACKGROUND OF THE INVENTION

Pyrazolo[1,5-a]pyrimidine is a commonly used scaffold in medicinal chemistry and derivatives thereof are known for their potent utility as analgesics, benzodiazepine receptor antagonists, angiotensin II receptor antagonists, angiogenesis inhibitors, anti-inflammatory agents, neuropeptide Y receptor antagonists, COX2-inhibitor and corticotrophin-releasing hormone receptor type 1 antagonists and as CHK1 inhibitors (e.g. Mayo et al (Adv. Synth. Catal. 2003, 345, 620-624; Tellew et al (Bioorg. Med. Chem. Lett. 2010, 20, 7259-7264); Chen et al (Bioorg. Med. Chem. Lett. 2004, 14, 3669-3673); Labroli et al (Bioorg. Med. Chem. Lett. 2011, 21, 471-474); Griffith et al (Bioorg. Med. Chem. Lett. 2011, 21, 2641-2645); Gilligan et al, (J. Med. Chem. 2009, 52, 3073-3083); He et al. (U.S. Pat. No. 6,313,124 B1); and Wren et al. (WO 2010/086040).

The scaffold has also been described in phosphatidylinositol 4-kinase (PI4K) inhibitors. Bianco et al (PLoS Pathogens, 2012, 8(3), 1-17) and LaMarche et al (Antimicr. Agents and Chemother. 2012, 56(10), 5149-5156) have shown that PI4K is important for hepatitis C virus (HCV) replication and Yang et al (J. Biol. Chem. 2012, 287(11), 8547-8467) have shown the same for coronavirus. McLeod et al (ACS Med. Chem. Lett. 2013, 4(7), 585-589) and van der Schaar et al (Antimicrobial Agents Chemother. 2013, 57(10), 4971-4981) have shown some imidazopyrazine derivatives inhibiting PI4K that are potent antivirals towards picornavirus.

Gudmundsson et al (Bioorg. Med. Chem. Lett. 2009, 19, 5689-5692) have disclosed some 3-arylpyrazolo[1,5-a]pyrimidines with potent activity against herpesviruses.

Hwang et al (Bioorg. Med. Chem. Lett. 2012, 22, 7297-7301) have described 3-arylpyrazolo[1,5-a]pyrimidines as PI4K inhibitors that have anti-HCV effects. Décor et al (Bioorg Med Chem Lett. 2013, 23, 3841-7) have also shown that PI4K is important for enterovirus replication. However, they have also shown that PI4K inhibitors (non 3-arylpyrazolo[1,5-a]pyrimidines and the 3-arylpyrazolo[1,5-a]pyrimidine 3-(3,4-dimethoxyphenyl)-2,5-dimethyl-N-(2-morpholinoethyl)pyrazolo[1,5-a]pyrimidin-7-amine (called T-00127-HEV1)) when tested in-vivo induced mortality in mice, which raised doubts on the safety of inhibiting PI4K.

In WO 2015/110491 certain 3-arylpyrazolo[1,5-a]pyrimidines are described as PI4K inhibitors for treatment of virus induced diseases.

Imidazo[1,2-b]pyridazine derivatives have been described as Mps1 kinase inhibitors (Kusakabe, J. Med. Chem. 2015, 58, 1760-1775). Similar scaffolds have been described as present in phosphatidylinositol 4-kinase (PI4K) inhibitors (McLeod et al (ACS Med. Chem. Lett. 2013, 4(7), 585-589) and van der Schaar et al (Antimicrobial Agents Chemother. 2013, 57(10), 4971-4981), and inhibitors of PI4K have been shown to be potent antivirals (Bianco et al, PLoS Pathogens, 2012, 8(3), 1-17; LaMarche et al, Antimicr. Agents and Chemother. 2012, 56(10), 5149-5156; Décor et al, Bioorg. Med. Chem. Lett. 2013, 23, 3841-7).

Autophagy is a process of homeostatic degradation in cells, used to create nutrients in times of stress and as a mechanism to recycle damaged organelles or microbes in the cytostol (Karanasios et al, 2016, Autophagy at the cell, tissue and organismal level (Springer)). Many pathogens interact with the host autophagic pathways and could impair the normal autophagy. Lai et al (Viruses, 2016, 8(32), 1-13) describe that viruses subvert the autophagy machinery to benefit the virus replication and exit from the host and that inhibition of PI4KIIIβ will have an effect on the autophagy processes and thus inhibit the virus replication. Sridhar et al (EMBO J. 2013, 32, 324-339) describe PI4KIIIβ to be a key factor in autophagy and it is believed that many diseases are caused by or linked to impaired or abnormal autophagy, for example neurodegenerative and neuropsychiatric diseases, cancer, cardiac diseases, inflammatory diseases and diabetes (Polajnar et al J. Cell. Mol. Med. 2014, 9(18). 1705-1711; Levine et al, Cell, 2008, 132(1), 27-42; Barlow, et al, DNA Cell. Biol, 2015, 34(4), 252-260). Cytochrome P450 3A4 (abbreviated CYP3A4) is one of the most important cytochrome P450 enzymes and is involved in the oxidative biotransformation of numerous clinically useful therapeutic agents. Therefore, inhibitors of CYP3A4 can affect the metabolism of a variety of drugs, increasing their bioavailability thereby causing adverse events due to unexpectedly high drug exposure. In patients receiving several different drugs in parallel it is necessary to avoid such drug-drug interaction, and this sometimes precludes the use of some otherwise therapeutically useful medicaments.

Consequently, there is a continued need for new medicaments that not only has the sought after therapeutic activity, but that also has no or little effect on the activity of enzymes involved in drug metabolism, in particular CYP3A4.

SUMMARY OF THE INVENTION

A first aspect is a compound of formula (I)

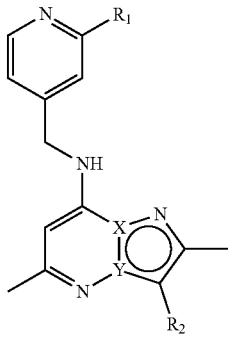

or a pharmaceutically acceptable salt thereof, wherein
one of X and Y is C and the other one is N;
$R_1$ is selected from halogen, CN, $NH(CH_3)$, $N(CH_3)_2$, C1-C4 alkoxy, optionally substituted by 1-3 halogens, and C1-C4 alkyl, which C1-C4 alkyl is optionally substituted by 1-3 halogens, CN, $NH(CH_3)$, or $N(CH_3)_2$; and
$R_2$ is 3,4-dimethoxyphenyl or 1,3-dimethyl-1H-indazol-5-yl.

The compound of formula (I) combines a high anti-viral activity with low, preferably essentially negligible, CYP3A4 inhibiting activity. Consequently, provided herein is a medicament of substantially reduced risk for drug-drug interaction.

A further aspect is a compound of formula (I), or a pharmaceutically acceptable salt thereof, for use in therapy.

A further aspect is a pharmaceutical composition comprising a compound of formula (I), or a pharmaceutically acceptable salt thereof, and optionally a pharmaceutically acceptable excipient.

A further aspect is a compound of formula (I), or a pharmaceutically acceptable salt thereof, for use in the treatment of a viral infection, e.g. an RNA viral infection.

A further aspect is the use of a compound of formula (I), or a pharmaceutically acceptable salt thereof, in the manufacture of a medicament for the treatment of a viral infection, e.g. an RNA viral infection.

A further aspect is a compound of formula (I), or a pharmaceutically acceptable salt thereof, capable of improving impaired or modulating abnormal autophagy in a cell, for use in the treatment of a disease as mentioned herein.

A further aspect is a compound of formula (I), or a pharmaceutically acceptable salt thereof, for use in the treatment of a disease linked to impaired or abnormal autophagy.

A further aspect is a compound of formula (I), or a pharmaceutically acceptable salt thereof, for use in the treatment of a disease linked to impaired autophagy.

A further aspect is a compound of formula (I), or a pharmaceutically acceptable salt thereof, for use in the treatment of a disease linked to abnormal autophagy.

A further aspect is a compound of formula (I), or a pharmaceutically acceptable salt thereof, for use in the treatment of a non-enveloped single-stranded (+) RNA viral infection.

A further aspect is a compound of formula (I), or a pharmaceutically acceptable salt thereof, for use in the treatment of an enteroviral infection, e.g. a picornaviral infection.

Still a further aspect is a compound of formula (I), or a pharmaceutically acceptable salt thereof, for use in the treatment of a disease selected from pancreatitis, poliomyelitis, encephalitis, meningitis, sepsis, cancer, such as breast, prostate, ovarian or colorectal cancer, paralysis, cardiac diseases, such as myocarditis, diabetes, common cold, hand-foot-and-mouth disease, herpangina, pleurodynia, diarrhea, mucocutaneous lesions, respiratory illness, conjunctivitis, myositis, chronic fatigue syndrome, neuropsychiatric diseases, and neurodegenerative diseases such as multiple sclerosis, Parkinson's disease, amyotrophic lateral sclerosis, Alzheimer's disease, and Huntington's disease, or inflammatory conditions.

A further aspect is a method for the treatment of a viral infection, e.g. an RNA viral infection by administration of a therapeutically effective amount of a compound of formula (I), or a pharmaceutically acceptable salt thereof, to a mammal in need of such treatment.

DETAILED DESCRIPTION OF THE INVENTION

Unless defined otherwise or clearly indicated by context, all technical and scientific terms and abbreviations used herein have the same meaning as commonly understood by one of ordinary skill in the art to which this disclosure belongs. However, definitions of some terms used herein will be given herein below.

"Pharmaceutically acceptable" means being useful in preparing a pharmaceutical composition that is generally safe, non-toxic and neither biologically nor otherwise undesirable and includes being useful for veterinary use as well as human pharmaceutical use.

The term "treating" (or "treatment") of a disease or disorder may refer to ameliorating the disease or disorder (i.e., arresting or reducing the development of the disease or at least one of the clinical symptoms thereof), and/or ameliorating at least one physical parameter, which may not be discernible by the patient. The term also may refer to inhibiting the disease or disorder, either physically, (e.g., stabilization of a discernible symptom), physiologically, (e.g., stabilization of a physical parameter), or both.

"Therapeutically effective amount" refers to an amount of a compound that, when administered to a patient for treating a disease, is sufficient to effect such treatment of the disease. The "therapeutically effective amount" will vary depending on the compound, the disease and its severity as well as the age, weight, etc., of the patient to be treated.

A "viral infection" refers to an infection by a virus, in a mammal.

An "RNA viral infection" refers to a viral infection wherein the virus has RNA (ribonucleic acid) as its genetic material.

A "non-enveloped single-stranded (+) RNA viral infection" refers to an infection by a non-enveloped single-stranded (+) RNA virus.

A "non-enveloped virus" is a virus lacking viral envelope.

A "single-stranded (+) RNA virus" is a virus having genetic material which is single-stranded RNA and which RNA can be immediately translated to viral protein by the cell infected by the virus.

By "abnormal autophagy" is meant e.g. autophagy that favours viral replication and release.

By "impaired autophagy" is meant a subnormally functioning autophagy in a cell.

A disease linked to impaired or abnormal autophagy that may be treated according to the invention e.g. may be selected from neurodegenerative and neuropsychiatric diseases, cancer, cardiac diseases, inflammatory diseases and diabetes, such as diseases mentioned herein.

The term "mammal" refers to a human or any mammalian animal, e.g. a primate, a farm animal, a pet animal, or a laboratory animal. Examples of such animals are monkeys, cows, sheep, goats, horses, pigs, dogs, cats, rabbits, mice, rats etc. Preferably, the mammal is a human. In some embodiments, however, the mammal is an animal, e.g. a farm animal, such as a cow, sheep, goat, horse, or pigs. In some other embodiments, the animal is a pet, e.g. a dog, a cat or a rabbit.

The term "excipient" refers to pharmaceutically acceptable chemicals, such as known to those of ordinary skill in the art of pharmacy to aid the administration of the medicinal agent. It is a compound that is useful in preparing a pharmaceutical composition, generally safe, non-toxic and neither biologically nor otherwise undesirable, and includes excipients that are acceptable for veterinary use as well as human pharmaceutical use. Exemplary excipients include binders, surfactants, diluents, disintegrants, antiadherents, and lubricants.

Unless otherwise stated or apparent from the context, the term "halogen" refers to F (fluoro), Cl (chloro), Br (bromo), or I (iodo).

Unless otherwise stated or apparent from the context, the term "Cm-Cn alkyl" denotes a straight or branched alkyl group having from m to n carbon atoms. For example, the term "C1-C4 alkyl" denotes a straight or branched alkyl group having from 1 to 4 carbon atoms. Such C1-C4 alkyl includes methyl, ethyl, n-propyl, iso-propyl, n-butyl, iso-butyl, sec-butyl, and t-butyl.

The term "Cm-Cn alkoxy" refers to a moiety of the formula

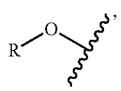

wherein R is Cm—Cn alkyl.

The term NH(CH$_3$) represents a moiety of formula

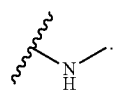

The term N(CH$_3$)$_2$ represents a moiety of formula

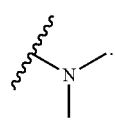 [SMILES: *N(C)C]

The term CN represents a moiety of formula

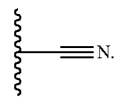

In a compound of formula (I), one of X and Y is C, and the other one is N. In some embodiments, X is C and Y is N, i.e. the compound is represented by formula (Ia)

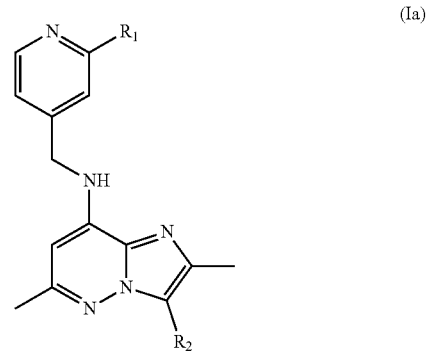

(Ia)

wherein R$_1$ and R$_2$ are as defined herein.

In some embodiments, X is N and Y is C, i.e. the compound is represented by formula (Ib)

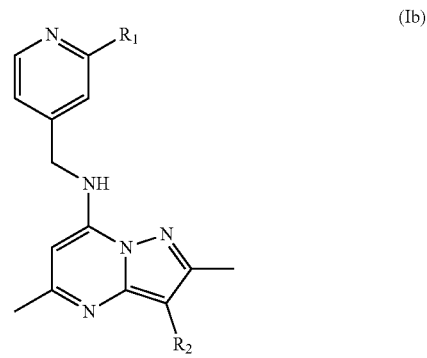

(Ib)

wherein R$_1$ and R$_2$ are as defined herein.

In a compound of formula (I), R$_1$ is selected from halogen, CN, NH(CH$_3$), N(CH$_3$)$_2$, C1-C4 alkoxy, optionally substituted by 1-3 halogens, and C1-C4 alkyl, optionally substituted by 1-3 halogens, CN, NH(CH$_3$), or N(CH$_3$)$_2$.

In some embodiments, R$_1$ is selected from halogen, CN, C1-C4 alkoxy, optionally substituted by 1-3 halogens, and C1-C4 alkyl, optionally substituted by 1-3 halogens.

In some embodiments, when R$_1$ is halogen, said halogen is selected from F, Cl, and Br. In some embodiments, said halogen is F or Cl. In some embodiments, said halogen is F.

In some embodiments, when R$_1$ is optionally substituted C1-C4 alkyl, said alkyl more particularly is C1-C3 alkyl. In some embodiments, said alkyl is methyl or ethyl. In some embodiments, said alkyl is methyl. In some embodiments, said alkyl is ethyl.

In some embodiments, when R$_1$ is optionally substituted C1-C4 alkyl, said alkyl is unsubstituted. In some other embodiments, said alkyl is substituted by 1-3 halogens, CN, NH(CH$_3$), or N(CH$_3$)$_2$. In some embodiments, when said alkyl is substituted by 1-3 halogens, said halogens are selected from F and Cl, in particular F. In some embodiments, said alkyl is said alkyl is substituted by 1-3 halogens, and/or by one substituent selected from CN, NH(CH$_3$), and N(CH$_3$)$_2$.

In some embodiments, when R$_1$ is substituted alkyl, any substituent on said alkyl is selected from halogen and CN. In some other embodiments, when R$_1$ is substituted alkyl, any substituent on said alkyl is selected from halogen, NH(CH$_3$), and N(CH$_3$)$_2$. In some other embodiments, when R$_1$ is substituted alkyl, any substituent on said alkyl is selected from NH(CH$_3$), and N(CH$_3$)$_2$. In some other embodiments, when R$_1$ is substituted alkyl, any substituent on said alkyl is selected from halogen, e.g. F and Cl, in particular F.

In some embodiments, when R$_1$ is C1-C4 alkoxy, said alkoxy more particularly is C1-C3 alkoxy. In some embodiments, said alkoxy is C1-C2 alkoxy. In some embodiments, said alkoxy is methoxy. In some embodiments, when R$_1$ is optionally substituted C1-C4 alkoxy said alkoxy is unsubstituted. In some other embodiments, said alkoxy is substituted by 1-3 halogens. In some embodiments, when said alkoxy is substituted by 1-3 halogens, any such halogen is selected from F and Cl, in particular F.

In some embodiments, R$_1$ is selected from halogen, CN, optionally substituted C1-C4 alkoxy, and optionally substituted C1-C4 alkyl. In some of these embodiments, R$_1$ is selected from halogen, optionally substituted C1-C3 alkoxy and optionally substituted C1-C3 alkyl, e.g. from F, Cl, CN, optionally substituted C1-C3 alkoxy and optionally substituted C1-C3 alkyl; or from F, Cl, CN, optionally substituted methoxy, and optionally substituted methyl and ethyl; or from F and optionally substituted methyl. In some of these embodiments, any substituent on any alkyl or alkoxy is F or Cl, in particular F. In some further of these embodiments, R$_1$ is selected from halogen, unsubstituted C1-C4 alkoxy and unsubstituted C1-C4 alkyl, e.g. from F, Cl, CN, C1-C3 alkoxy and C1-C3 alkyl; or from F, Cl, CN, methoxy, methyl and ethyl; or from F and methyl.

In some embodiments, R$_1$ is selected from halogen and optionally substituted C1-C4 alkyl. In some of these embodiments, R$_1$ is selected from halogen and optionally substituted C1-C3 alkyl, e.g. from F, Cl, and optionally substituted C1-C3 alkyl; or from F, Cl, and optionally substituted methyl or ethyl; or from F, and optionally substituted methyl or ethyl; or from F and optionally substituted methyl. In some of these embodiments, any substituent on the alkyl is F or Cl, in particular F. In some further of these embodiments, R$_1$ is selected from halogen and unsubstituted C1-C4 alkyl, e.g. from F, Cl, and C1-C3 alkyl; or from F, Cl, methyl and ethyl; or from F, methyl and ethyl; or from F and methyl.

In some other embodiments, R$_1$ is selected from halogen, unsubstituted C1-C4 alkyl and unsubstituted C1-C4 alkoxy, e.g. from F, Cl, C1-C3 alkyl and C1-C3 alkoxy; or from F, Cl, methyl, ethyl, and methoxy; or from F, methyl, ethyl, and methoxy; or from F, methyl, and methoxy; or from methyl and methoxy.

In some embodiments, R$_1$ is selected from optionally substituted C1-C4 alkyl, and optionally substituted C1-C4 alkoxy. In some embodiments, R$_1$ is selected from unsubstituted C1-C4 alkyl, and unsubstituted C1-C4 alkoxy. In still other embodiments, R$_1$ is selected from optionally substituted C1-C4 alkyl, and unsubstituted C1-C4 alkoxy. In still other embodiments, R$_1$ is selected from C1-C4 alkyl and C1-C4 alkoxy, said alkoxy and alkyl optionally being substituted by 1-3 halogens, e.g. 1-3 halogens selected from F and Cl, in particular 1-3 F. In some embodiments, R$_1$ is selected from methyl, ethyl, trifluoromethyl and methoxy.

In still other embodiments, R$_1$ is selected from halogen, e.g. R$_1$ is F or Cl, in particular F.

In still some further embodiments, R$_1$ is selected from F, CN, methoxy, methyl, trifluoromethyl, and ethyl; e.g. from F, methyl, trifluoromethyl, and ethyl.

In a compound of formula (I), R$_2$ is 3,4-dimethoxyphenyl or 1,3-dimethyl-1H-indazol-5-yl, i.e. R$_2$ is a moiety of formula (II) or (III)

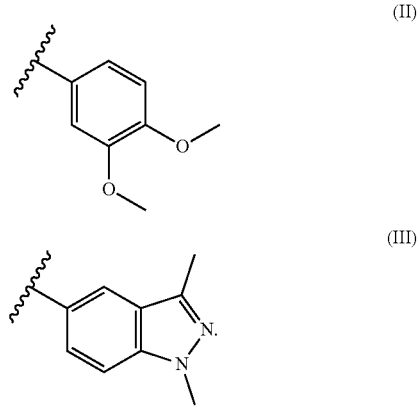

In some embodiments, R$_2$ is 3,4-dimethoxyphenyl, i.e. a moiety of formula (II), and the compound provided herein may be represented by formula (Ic)

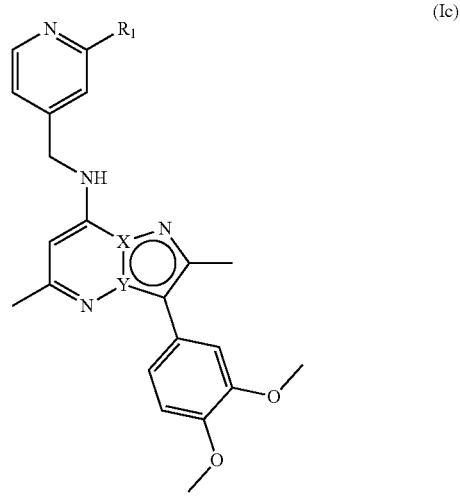

wherein X, Y and R$_1$ are as defined herein.

In some other embodiments, R₂ is 1,3-dimethyl-1H-indazol-5-yl, i.e. a moiety of formula (III), and the compound provided herein may be represented by formula (Id)

In some other embodiments of a compound of formula (Ic), X is N and Y is C, i.e. the compound may be represented by formula (If)

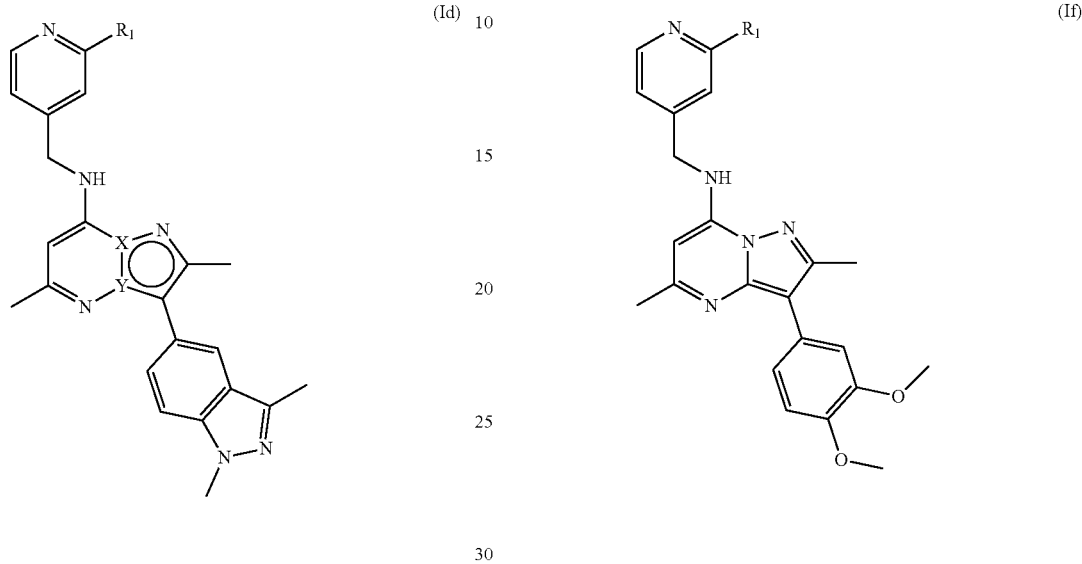

wherein X, Y and R₁ are as defined herein.

In some embodiments of a compound of formula (Ic), X is C and Y is N, i.e. the compound may be represented by formula (Ie)

wherein R₁ is as defined herein.

In some embodiments of a compound of formula (Id), X is C and Y is N, i.e. the compound may be represented by formula (Ig)

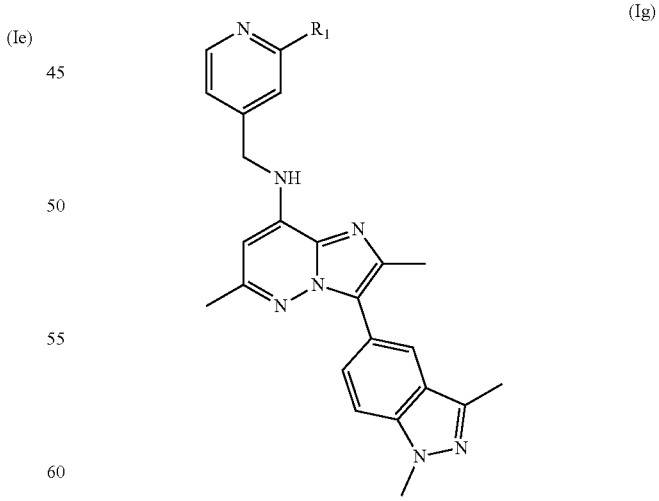

wherein R₁ is as defined herein.

wherein R₁ is as defined herein.

In some other embodiments of a compound of formula (Id), X is N and Y is C, i.e. the compound may be represented by formula (Ih)

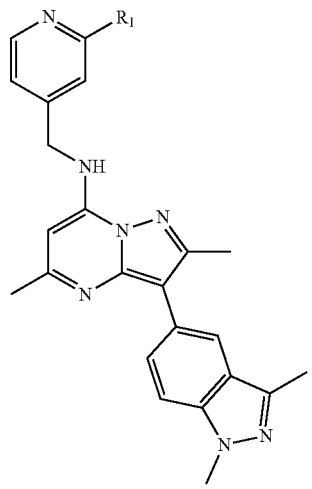

(Ih)

wherein $R_1$ is as defined herein.

Unless otherwise specified or apparent from the context, any reference to a compound of formula (I) also should be construed as a reference to a compound as represented by any of the formulas (Ia), (Ib), (Ic), (Id), (Ie), (If), (Ig), and (Ih).

In some embodiments, a compound of formula (I) more particularly is a compound of formula (Ie) or (Ih), i.e. a compound of formula (I)

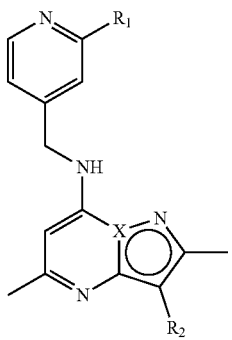

(I)

or a pharmaceutically acceptable salt thereof, wherein
$R_1$ is as defined herein; and
X is C, Y is N, and $R_2$ is 3,4-dimethoxyphenyl; or
X is N, Y is C, and $R_2$ is 21,3-dimethyl-1H-indazol-5-yl.

The compounds of formula (I) also may be transformed into suitable, pharmaceutically acceptable salts. The term pharmaceutically acceptable salt of a compound refers to a salt that is pharmaceutically acceptable, as defined herein, and that possesses the desired pharmacological activity of the parent compound. Pharmaceutically acceptable salts include acid addition salts formed with inorganic acids, e.g. hydrochloric acid, hydrobromic acid, sulphuric acid, nitric acid, phosphoric acid; or formed with organic acids, e.g. acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, etc.

In the preparation of acid addition salts, preferably such acid are used which form suitably therapeutically acceptable salts. Examples of such acids are hydrohalogen acids, sulfuric acid, phosphoric acid, nitric acid, aliphatic, alicyclic, aromatic or heterocyclic carboxylic or sulfonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybenzoic acid, embonic acid, methanesulfonic acid, ethanesulfonic acid, hydroxyethanesulfonic acid, halogenbenzenesulfonic acid, toluenesulfonic acid or naphthalenesulfonic acid.

Whenever a chiral atom is present in a chemical structure, it is intended that all stereoisomers associated with that chiral atom are encompassed by the structure, unless otherwise specified. Using the Cahn-Ingold-Prelog RS notational system, any asymmetric atom may be present in the (R)- or (S)-configuration, and the compound may be present as a mixture of its stereoisomers, e.g. a racemic mixture, or one stereoisomer only, each being within the scope of the present invention.

The present invention includes pharmaceutical compositions comprising a compound of formula (I), or an individual isomer, racemic or non-racemic mixture of isomers or a pharmaceutically acceptable salt thereof, together with at least one pharmaceutically acceptable excipient, e.g. a carrier, and optionally other therapeutic and/or prophylactic ingredients.

The present invention includes pharmaceutical compositions comprising at least one compound of formula (I), or an individual isomer, racemic or non-racemic mixture of isomers or a pharmaceutically acceptable salt thereof, together with at least one pharmaceutically acceptable excipient, e.g. a carrier, and optionally other therapeutic and/or prophylactic ingredients.

A pharmaceutical composition according to the invention may be for topical (local) or systemic administration, e.g. for enteral administration, such as rectal or oral administration, or for parenteral administration to a mammal (especially a human), and comprises a therapeutically effective amount of a compound according to the invention or a pharmaceutically acceptable salt thereof, as active ingredient, in association with a pharmaceutically acceptable excipient, e.g. a pharmaceutically acceptable carrier. The therapeutically effective amount of the active ingredient is as defined herein above and depends e.g. on the species of mammal, the body weight, the age, the individual condition, individual pharmacokinetic data, the disease to be treated and the mode of administration.

For enteral, e.g. oral, administration, the compounds of the invention may be formulated in a wide variety of dosage forms. The pharmaceutical compositions and dosage forms may comprise a compound or compounds of the present invention or pharmaceutically acceptable salt(s) thereof as the active component. The pharmaceutically acceptable carriers may be either solid or liquid. Solid form preparations include powders, tablets, pills, lozenges, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The formulation of the active compound may comprise an encapsulating material as carrier, providing a capsule in which the active component, with or without carriers, is surrounded by a carrier, which is in association with it.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well-known suspending agents. Solid form preparations include solutions, suspensions, and emulsions, and may contain, in addition to the active component, colorants, flavors, stabilizers, buffers, artificial and natural sweeteners, dispersants, thickeners, solubilising agents, and the like.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

The compounds of the invention also may be administered parenterally, e.g. by inhalation, injection or infusion, e.g. by intravenous, intraarterial, intraosseous, intramuscular, intracerebral, intracerebroventricular, intrasynovial, intrasternal, intrathecal, intralesional, intracranial, intracutaneous and subcutaneous injection or infusion.

Thus, for parenteral administration, the pharmaceutical compositions of the invention may be in the form of a sterile injectable or infusible preparation, for example, as a sterile aqueous or oleaginous suspension. This suspension may be formulated according to techniques known in the art using suitable dispersing or wetting agents (e.g., Tween 80), and suspending agents. The sterile injectable or infusible preparation may also be a sterile injectable or infusible solution or suspension in a non-toxic parenterally acceptable diluent or solvent. For example, the pharmaceutical composition may be a solution in 1,3-butanediol. Other examples of acceptable vehicles and solvents that may be employed in the compositions of the present invention include, but are not limited to, mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant.

Solutions for parenteral use also may contain suitable stabilizing agents, and if necessary, buffer substances. Suitable stabilizing agents include antioxidizing agents, such as sodium bisulfate, sodium sulfite or ascorbic acid, either alone or combined, citric acid and its salts and sodium EDTA. Parenteral solutions may also contain preservatives, such as benzalkonium chloride, methyl- or propyl-paraben, and cholorobutanol.

For inhalation or nasal administration, suitable pharmaceutical formulations are as particles, aerosols, powders, mists or droplets, e.g. with an average size of about 10 µm in diameter or less. For example, compositions for inhalation may be prepared as solutions in saline, employing benzyl alcohol or other suitable preservatives, absorption promoters to enhance bioavailability, fluorocarbons, and/or other solubilising or dispersing agents known in the art.

In some embodiments, the formulation of the invention is a liposomal formulation. Liposomal formulations are well-known within the pharmaceutical fields, and are described e.g. in Remington, Essentials of Pharmaceutics, Ed. Linda Felton (Pharmaceutical Press 2012), pages 456-7 and in numerous other publications. Information on e.g. choice of suitable liposome formulations, suitable lipids, preparation methods, etc. is easily available to the person of ordinary skill in the art. Examples of lipids for liposome formation are phospholipids, sphingolipids, sterol lipids, and fatty acids. Lipids suitable for liposome formation may be purchased e.g. from Avanti® Polar Lipids, Inc.

The pharmaceutical compositions of the invention may also be administered topically, to the skin or to a mucous membrane. For topical application, the pharmaceutical composition may be e.g. a lotion, a gel, a paste, a tincture, a transdermal patch, or a gel for transmucosal delivery.

The composition may be formulated as a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water.

Alternatively, the pharmaceutical composition may be formulated as a suitable lotion or cream containing the active compound suspended or dissolved in a carrier. Suitable carriers include, but are not limited to, mineral oil, sorbitan monostearate, polysorbate 60, cetyl esters wax, cetaryl alcohol, 2-octyldodecanol, benzyl alcohol and water.

The pharmaceutical compositions of this invention may also be topically applied to the lower intestinal tract by rectal suppository formulation or in a suitable enema formulation.

Suitable pharmaceutical excipients, e.g. carriers, and methods of preparing pharmaceutical dosage forms are described in Remington's Pharmaceutical Sciences, Mack Publishing Company, a standard reference text in art of drug formulation.

The pharmaceutical compositions may comprise from approximately 1% to approximately 95%, preferably from approximately 20% to approximately 90% of a compound of formula (I), together with at least one pharmaceutically acceptable excipient. In general, the compounds of the invention will be administered in a therapeutically effective amount by any of the accepted modes of administration for agents that serve similar utilities. Suitable daily dosages typically ranges from 1 to 1000 mg, e.g. 1-500 mg daily, or 1-50 mg daily, depending upon numerous factors such as the severity of the disease to be treated, the age and relative health of the patient, the potency of the compound used, the route and form of administration, and the indication towards which the administration is directed, etc. One of ordinary skill in the art of treating such diseases will be able, without undue experimentation and in reliance upon personal knowledge and the disclosure of this application, to ascertain a therapeutically effective amount of the compounds of the present invention for a given disease. Compounds of the invention may be administered as pharmaceutical formulations including those suitable for enteral or parenteral administration. The preferred manner of administration is generally oral using a convenient daily dosage regimen which can be adjusted according to the degree of affliction.

The compound of the present invention is contemplated as useful for the treatment of diseases caused by RNA viral infection in a mammal, e.g. non-enveloped single-stranded (+) RNA viral infection, in particular diseases caused by picornaviruses.

The picornavirus e.g. may be a Parechovirus (e.g. Ljungan or Parecho), a Cardiovirus (e.g. EMCV or Theiler's virus), Enterovirus (e.g. EV, Coxsackie, Polio, Rhino) or a hepatovirus. For veterinary use, the picornavirus may be e.g. an Aphthovirus or a Teschovirus.

Diseases that are considered to be linked to, caused by, or otherwise associated with virus infection, e.g. by picornaviruses, are e.g. neurodegenerative diseases such as multiple sclerosis, Parkinson's disease, amyotrophic lateral sclerosis, Alzheimer's disease, Huntington's disease, poliomyelitis, encephalitis, meningitis, sepsis, cancer, paralysis, myocarditis, diabetes, common cold, hand-foot-and-mouth disease, herpangina, pleurodynia, diarrhea, mucocutaneous lesions, respiratory illness, conjunctivitis, myositis, and chronic fatigue syndrome.

It is considered to be well within the knowledge of the person of ordinary skill in the art to synthesize and identify compounds of formula (I) as defined herein, by following methods as generally described in the below non-limiting examples, and the general methods described in literature, e.g. in PCT/EP2018/058522 (published as WO 2018/185120 A1), and PCT/EP2015/051177 (published as WO 2015/110491 A2), the contents of which applications are incorporated herein by reference.

EXAMPLES

General Procedures

Reactions were performed in flame-dried sealed-tubes or oven-dried glassware under a positive pressure of argon or nitrogen, unless otherwise noted. Air- and moisture-sensitive liquids and solutions were transferred via syringe. Tetrahydrofuran (THF) was distilled from sodium/benzophenone-ketyl. Dichloromethane ($CH_2Cl_2$) was distilled from calcium hydride. All other chemicals were obtained from commercial vendors and were used without further purification unless noted otherwise. Molecular sieves were activated at 350° C. and were crushed immediately prior to use, then flame-dried under vacuum. Reactions were monitored by thin layer chromatography (TLC) with 0.25-mm E. Merck pre-coated silica gel plates. Organic solutions were concentrated by rotary evaporation below 50° C. Flash column chromatography was performed employing 60-120, 230-400 mesh silica gel and neutral alumina. Yields refer to chromatographically and spectroscopically pure compounds unless otherwise noted.

Instrumentation $^1H$ and $^{13}C$ spectra were recorded either on a Bruker AVANCE III HD 400 MHz spectrometer or Bruker AVANCE II 300 MHz spectrometer. Chemical shifts are expressed in parts per million (δ scale) downfield from tetramethylsilane and are referenced to the residual resonance in the NMR solvent ($CHCl_3$: δ 7.26 for 1H NMR, δ 77.16 for 13C NMR). LC-MS was performed on an Agilent XCT Ion Trap equipped with chemstation and Bruker daltonics software.

Synthesis of 3-(3,4-dimethoxyphenyl)-8-iodo-2,6-dimethylimidazo[1,2-b]pyridazine The synthetic intermediary 3-(3,4-dimethoxyphenyl)-8-iodo-2,6-dimethylimidazo[1,2-b]pyridazine was synthesized in a multistep process as follows:

Step 1: 2,6-dimethylimidazo[1,2-b]pyridazine

To a stirred solution of 6-methylpyridazine-3-ylamine (50 g, 455.3 mmol) in ethanol (500 mL) was added chloroacetone (58 ml, 683 mmol) and the solution was heated at 85° C. for 10 h. Upon completion, the ethanol in the reaction was distilled out. The obtained crude product was purified by flash column chromatography (neutral alumina) eluting the required compound, 2,6-dimethylimidazo[1,2-b]pyridazine (36 g, 53.4%) with 10% ethylacetate-hexanes as a dark brown solid.

Step 2: 3-bromo-2,6-dimethylimidazo[1,2-b]pyridazine

To a stirred solution of 2,6-dimethylimidazo[1,2-b]pyridazine (36 g, 244.5 mmol) in acetonitrile (360 mL) was added N-bromosuccinimide (NBS) (52.2 g, 293.4 mmol) and stirred at ambient temperature for 1 h. Upon completion, the acetonitrile in the reaction was distilled out. The obtained crude product was purified by flash column chromatography (neutral alumina) eluting the required compound 3-bromo-2,6-dimethylimidazo[1,2-b]pyridazine (18 g, 32.5%) with 15% ethylacetate-hexanes as a solid.

Step 3: 3-(3,4-dimethoxyphenyl)-2,6-dimethylimidazo[1,2-b]pyridazine

A 100 ml round bottom flask was charged with 3-bromo-2,6-dimethylimidazo[1,2-b]pyridazine (5 g, 17.6 mmol), boronic ester (4.4 g, 19.4 mmol), potassium carbonate (7.5 g, 54.3 mmol) and dioxan:water (45 ml:5 ml). This solution was degassed with $N_2$ for 10 min and then the [1,1'-bis (diphenylphosphino)ferrocene]dichloropalladium(II). dichloromethane complex ($Pd(dppf)Cl_2.DCM$ complex) (1.8 g, 2.2 mmol) was added. The reaction was heated at 100° C. for 16 h. Upon completion, the reaction was diluted with ethylacetate and filtered through a celite bed. The filtrate was partitioned between ethylacetate and water. The ethylacetate layer was dried over $Na_2SO_4$ and concentrated under reduced pressure. The obtained crude product was purified by flash column chromatography (neutral alumina) eluting the required compound 3-(3,4-dimethoxyphenyl)-2, 6-dimethylimidazo[1,2-b]pyridazine (4.2 g, 67.7%) with 30% ethylacetate-hexanes as an off-white solid.

Step 4: 3-(3,4-dimethoxyphenyl)-8-iodo-2,6-dimethylimidazo[1,2-b]pyridazine

To a stirred solution of 2M lithium diisopropylamide (LDA) (0.7 ml, 1.4 mmol) in THF at −78° C. was added a solution of 3-(3,4-dimethoxyphenyl)-2,6-dimethylimidazo[1,2-b]pyridazine (0.2 g, 0.705 mmol) dissolved in THF (5 mL), dropwise. After 10 min, iodine (0.178 g, 0.705 mmol) dissolved in THF (3 mL) was added and the reaction was stirred at ambient temperature for 1 h. Upon completion, the reaction was quenched with saturated NH$_4$Cl solution and extracted with ethylacetate. The ethylacetate layers were dried under Na$_2$SO$_4$ and concentrated under reduced pressure. The obtained crude product was purified by flash column chromatography (neutral alumina) eluting the required compound 3-(3,4-dimethoxyphenyl)-8-iodo-2,6-dimethylimidazo[1,2-b]pyridazine (30 mg, 10.7%) with 30% ethylacetate-hexanes as a pale yellow solid.

Example 1

3-(3,4-dimethoxyphenyl)-2,6-dimethyl-N-((2-methylpyridin-4-yl)methyl)imidazo[1,2-b]pyridazin-8-amine

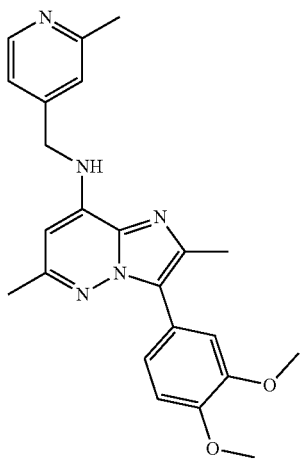

To a stirred solution of 3-(3,4-dimethoxyphenyl)-8-iodo-2,6-dimethylimidazo[1,2-b]pyridazine (0.1 g, 0.240 mmol) and amine (0.06 g, 0.312 mmol) in toluene (2 mL) was added cesium carbonate (0.156 g, 0.48 mmol), 2,2'-bis(diphenylphosphino)-1,1'-binaphthyl (BINAP (7 mg, 0.012 mmol) and Pd(OAc)$_2$ (2 mg, 0.012 mmol). The reaction was stirred at 105° C. for 16 h. Upon completion, the reaction was diluted with 10% MeOH—CH$_2$Cl$_2$ and filtered through a celite bed. The filtrate was concentrated and the obtained solid was washed with acetonitrile to afford Ex 0.2 (0.09 g, 91.83%) as a pale brown solid.

Example 2

3-(3,4-dimethoxyphenyl)-N-((2-fluoropyridin-4-yl)methyl)-2,6-dimethylimidazo[1,2-b]pyridazin-8-amine

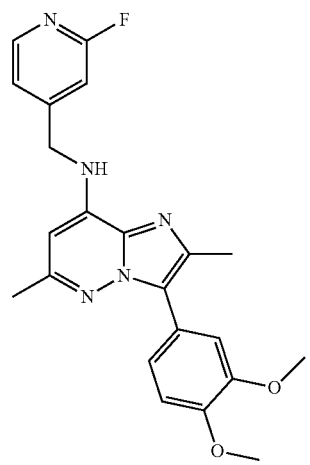

To a stirred solution of 3-(3,4-dimethoxyphenyl)-8-iodo-2,6-dimethylimidazo[1,2-b]pyridazine (0.15 g, 0.360 mmol) and amine (0.093 g, 0.46 mmol) in toluene (3 mL) was added cesium carbonate (0.23 g, 0.72 mmol), 2,2'-bis(diphenylphosphino)-1,1'-binaphthyl (BINAP) (11 mg, 0.018 mmol) and Pd(OAc)$_2$ (4 mg, 0.018 mmol). The reaction was stirred at 105° C. for 16 h. Upon completion, the reaction was diluted with 10% MeOH—CH$_2$Cl$_2$ and filtered through a celite bed. The filtrate was concentrated and the obtained solid was washed with acetonitrile to afford Ex. 1 (0.120 g, 80%) as a pale brown solid.

Synthesis of 7-chloro-3-iodo-2,5-dimethylpyrazolo[1,5-a]pyrimidine

The synthetic intermediary 7-chloro-3-iodo-2,5-dimethylpyrazolo[1,5-a]pyrimidine was synthesized in a multistep process as follows:

Step 1: 2,5-dimethylpyrazolo[1,5-a]pyrimidin-7-ol

A round bottom flask was charged with 3-amino-5-methylpyrazole (100 g, 1.02 mol), ethyl acetoacetate (161 mL, 1.23 mol), acetic acid (300 mL) and 1,4-dioxan (1000 mL). The reaction was refluxed for 16 h at 105° C. Off-white solids were obtained upon completion of the reaction and were filtered through suction. The solids were washed with cold hexane and dried under vacuum to obtain 2,5-dimethylpyrazolo[1,5-a]pyrimidin-7-ol (85 g, 49%) as an off-white solid.

Step 2: 7-chloro-2,5-dimethylpyrazolo[1,5-a]pyrimidine

To a solution of 2,5-dimethylpyrazolo[1,5-a]pyrimidin-7-ol (120 g, 0.73 mol) in acetonitrile (1200 mL) was added POCl$_3$ (103 ml, 1.1 mol) dropwise. Upon completion of addition, the reaction was heated at 80° C. for 12 h. Upon completion, the POCl$_3$ in the reaction was distilled out. The crude product was diluted with water and neutralized with saturated NaHCO₃ solution and extracted with ethyl acetate. The organic layer was dried over sodium sulfate and concentrated under reduced pressure. The crude product was purified by flash column chromatography eluting the 7-chloro-2,5-dimethylpyrazolo[1,5-a]pyrimidine with 20% ethylacetate-hexanes as an off-white solid (108 g, 80.8%).

Step 3: 7-chloro-3-iodo-2,5-dimethylpyrazolo[1,5-a]pyrimidine

To an ice cold solution of 7-chloro-2,5-dimethylpyrazolo[1,5-a]pyrimidine (120 g, 0.66 mol) in acetonitrile (1200 mL) at −10° C. was added N-iodosuccinimide (163.5 g, 0.726 mol) portion wise. The reaction was stirred at this temperature for 1 h. Upon completion, solids were observed. The reaction was quenched with ice cold water and filtered via suction. The obtained solids were washed with hexane and dried under vacuum to afford 7-chloro-3-iodo-2,5-dimethylpyrazolo[1,5-a]pyrimidine as a white solid (182.8 g, 89.9%).

Synthesis of 1,3-dimethyl-5-(4,4,5,5-tetramethyl-[1,3,2]dioxaborolan-2-yl)-1H-indazol The boronic ester 1,3-dimethyl-5-(4,4,5,5-tetramethyl-[1,3,2]dioxaborolan-2-yl)-1H-indazol was synthesized in a multistep process as follows:

Step 1: 5-bromo-1,3-dimethyl-1H-indazole

A stirred solution of 1-(5-bromo-2-fluorophenyl)ethanone (50 g, 230 mmol) and N-methyl hydrazine (42.4 mL, 805 mmol) in pyridine (500 mL) was heated at 90° C. for 10 h. Upon completion, the pyridine in the reaction was distilled out. The crude product was partitioned between water and ethylacetate. The ethylacetate layers were dried over sodium sulfate and concentrated. The obtained crude product was purified by flash column chromatography (neutral alumina) eluting the required compound 5-bromo-1,3-dimethyl-1H-indazole (20.23 g, 41.8%) with 2% ethylacetate-hexanes as a pale brown viscous compound.

Step 2: 1,3-dimethyl-5-(4,4,5,5-tetramethyl-[1,3,2]dioxaborolan-2-yl)-1H-indazole To a solution of 5-bromo-1,3-dimethyl-1H-indazole (26 g, 115 mmol) and bispinacolato diboron (32.3 g, 127 mmol) in 1,4-dioxan (260 mL) was added KOAc (34 g, 345 mmol). The reaction was degassed with N₂ for 10 min and then Pd(PPh₃)₄ (6.6 g, 5.57 mmol) was added and heated at 95° C. for 16 h. Upon completion of addition, the reaction was heated at 80° C. for 12 h. Upon completion, the reaction was filtered through celite, the filtrate was concentrated. The obtained crude product was purified by flash column chromatography (neutral alumina) eluting the required compound 1,3-dimethyl-5-(4,4,5,5-tetramethyl-[1,3,2]dioxaborolan-2-yl)-1H-indazole (18 g, 52.1%) with 5% ethylacetate-hexanes as an off-white solid compound.

Example 3

3-(1,3-dimethyl-1H-indazol-5-yl)-2,5-dimethyl-N-[(2-fluoropyridin-4-yl)methyl]pyrazolo[1,5-a]pyrimidin-7-amine

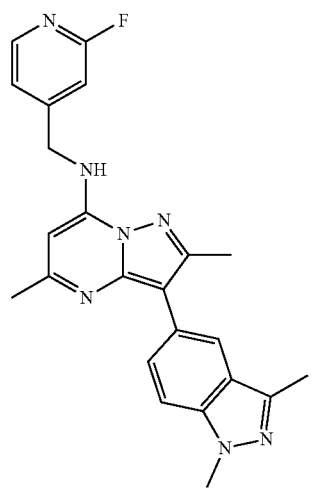

Step 1: N-[(2-fluoropyridin-4-yl)methyl]-3-iodo-2,5-dimethylpyrazolo[1,5-a]pyrimidin-7-amine To a stirred solution of 7-chloro-3-iodo-2,5-dimethylpyrazolo[1,5-a]pyrimidine (1.1 g, 3.57 mmol) and 1-(2-fluoropyridin-4-yl)methanamine (0.586 g, 4.6 mmol) in ethanol (5.5 mL) was added diisopropylethylamine (5.5 mL, 5 Vols) and stirred at 80° C. for 6 h. Upon completion, the ethanol in the reaction was distilled out. The crude product was partitioned between water and ethylacetate. The ethylacetate layers were dried over sodium sulfate and concentrated under reduced pressure. Flash column chromatography eluted the required compound with 35% ethylacetate-hexane. Upon concentration it afforded N-[(2-fluoropyridin-4-yl)methyl]-3-iodo-2,5-dimethylpyrazolo[1,5-a]pyrimidin-7-amine (0.9 g, 63.82%) as a pale yellow compound.

Step 2: tert-butyl [(2-fluoropyridin-4-yl)methyl](3-iodo-2,5-dimethylpyrazolo[1,5-a]pyrimidin-7-yl)carbamate To a stirred solution of N-[(2-fluoropyridin-4-yl)methyl]-3-iodo-2,5-dimethylpyrazolo[1,5-a]pyrimidin-7-amine (0.5 g, 1.26 mmol) in dichloromethane (DCM) (5 mL) was added 4-dimethylaminopyridine (DMAP) (0.153 g, 1.26 mmol) at 0° C. Then Boc anhydride (di-tert-butyl dicarbonate) (0.33 ml, 1.51 mmol) was added dropwise at this temperature and stirred at ambient temperature for 2 h. Upon completion, the reaction was washed with water. The organic layer was dried over Na₂SO₄ and concentrated. The obtained crude product was purified by flash column chromatography (neutral alumina) eluting the required compound tert-butyl [(2-fluoropyridin-4-yl)methyl](3-iodo-2,5-dimethylpyrazolo[1,5-a]pyrimidin-7-yl)carbamate (0.51 g, 82.2%) with 10% ethylacetate-hexanes as an off-white solid.

Step 3: [3-(1,3-Dimethyl-1H-indazol-5-yl)-2,5-dimethyl-pyrazolo[1,5-a]pyrimidin-7-yl]-(2-fluoro-pyridin-4-ylmethyl)-carbamic acid tert-butyl ester A 25 ml round bottom flask was charged with tert-butyl [(2-fluoropyridin-4-yl)methyl](3-iodo-2,5-dimethylpyrazolo[1,5-a]pyrimidin-7-yl)carbamate (0.45 g, 0.904 mmol), 1,3-dimethyl-5-(4,4,5,5-tetramethyl-[1,3,2]dioxaborolan-2-yl)-1H-indazole (0.322 g, 1.17 mmol), potassium carbonate (0.311 g, 2.26 mmol) and dioxan:water (4.5 mL:0.5 mL). This solution was degassed with $N_2$ for 10 min and then the Pd(dppf)Cl$_2$.DCM complex (0.110 g, 0.135 mmol) was added. The reaction was heated at 100° C. for 16 h. Upon completion, the reaction was diluted with ethylacetate and filtered through a celite bed. The filtrate was partitioned between ethylacetate and water. The ethylacetate layer was dried over $Na_2SO_4$ and concentrated under reduced pressure. The obtained crude product was purified by flash column chromatography (neutral alumina) eluting the required compound [3-(1,3-Dimethyl-1H-indazol-5-yl)-2,5-dimethyl-pyrazolo[1,5-a]pyrimidin-7-yl]-(2-fluoro-pyridin-4-ylmethyl)-carbamic acid tert-butyl ester (0.2 g, 42.9%) with 30% ethylacetate-hexanes as an off-white solid.

Step 4: 3-(1,3-dimethyl-1H-indazol-5-yl)-2,5-dimethyl-N-[(2-fluoropyridin-4-yl)methyl]pyrazolo[1,5-a]pyrimidin-7-amine To an ice cold solution of [3-(1,3-Dimethyl-1H-indazol-5-yl)-2,5-dimethyl-pyrazolo[1,5-a]pyrimidin-7-yl]-(2-fluoro-pyridin-4-ylmethyl)-carbamic acid tert-butyl ester (0.2 g, 0.388 mmol) in dichloromethane (2 mL) was added TFA (2 mL) dropwise. After completion of addition, the reaction mass was stirred at ambient temperature for 6 h. After completion of the reaction, the solvent and excess TFA were distilled out. The crude product was basified with 1N NaOH solution and extracted with 10% MeOH-DCM. The organic layers were dried over $Na_2SO_4$ and concentrated. The obtained crude product was purified by flash column chromatography (neutral alumina) eluting the required compound Ex. 3 (0.06 g, 37.5%) with 70% ethylacetate-hexanes as an off-white solid.

Example 4

3-(1,3-dimethyl-1H-indazol-5-yl)-2,5-dimethyl-N-[(2-methylpyridin-4-yl)methyl]pyrazolo[1,5-a]pyrimidin-7-amine

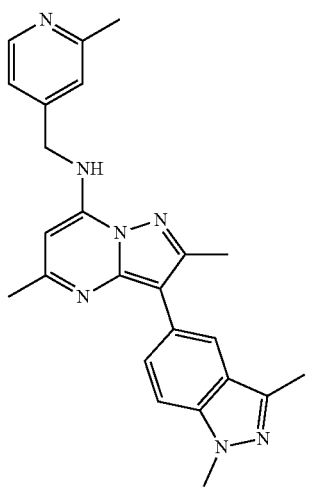

Step 1: 3-iodo-2,5-dimethyl-N-[(2-methylpyridin-4-yl)methyl]pyrazolo[1,5-a]pyrimidin-7-amine To a stirred solution of 7-chloro-3-iodo-2,5-dimethylpyrazolo[1,5-a]pyrimidine (1.1 g, 3.57 mmol) and 1-(2-methylpyridin-4-yl)methanamine (0.586 g, 4.6 mmol) in ethanol (5.5 ml) was added diisopropylethylamine (5.5 mL, 5 Vols) and stirred at 80° C. for 6 h. Upon completion, the ethanol in the reaction was distilled out. The crude product was partitioned between water and ethylacetate. The ethylacetate layers were dried over sodium sulfate and concentrated under reduced pressure. Flash column chromatography eluted the required compound with 35% ethylacetate-hexane. Upon concentration it afforded 3-iodo-2,5-dimethyl-N-[(2-methylpyridin-4-yl)methyl]pyrazolo[1,5-a]pyrimidin-7-amine (0.9 g, 40.1%) as a pale yellow compound.

Step 2: (3-iodo-2,5-dimethyl-pyrazolo[1,5-a]pyrimidin-7-yl)-(2-methyl-pyridin-4-ylmethyl)-carbamic acid tert-butyl ester To a stirred solution of 3-iodo-2,5-dimethyl-N-[(2-methylpyridin-4-yl)methyl]pyrazolo[1,5-a]pyrimidin-7-amine (0.5 g, 1.26 mmol) in dichloromethane (5 mL) was added DMAP (0.153 g, 1.26 mmol) at 0° C. Then Boc anhydride (0.33 ml, 1.51 mmol) was added dropwise at this temperature and stirred at ambient temperature for 2 h. Upon completion, the reaction was washed with water. The organic layer was dried over $Na_2SO_4$ and concentrated. The obtained crude product was purified by flash column chromatography (neutral alumina) eluting the required compound (3-iodo-2,5-dimethyl-pyrazolo[1,5-a]pyrimidin-7-yl)-(2-methyl-pyridin-4-ylmethyl)-carbamic acid tert-butyl ester (0.51 g, 82.2%) with 10% ethylacetate-hexanes as an off-white solid.

Step 3: [3-(1,3-Dimethyl-1H-indazol-5-yl)-2,5-dimethyl-pyrazolo[1,5-a]pyrimidin-7-yl]-(2-methyl-pyridin-4-ylmethyl)-carbamic acid tert-butyl ester A 25 ml round bottom flask was charged with (3-Iodo-2,5-dimethyl-pyrazolo[1,5-a]pyrimidin-7-yl)-(2-methyl-pyridin-4-ylmethyl)-carbamic acid tert-butyl ester (0.45 g, 0.904 mmol), 1,3-dimethyl-5-(4,4,5,5-tetramethyl-[1,3,2]dioxaborolan-2-yl)-1H-indazole (0.322 g, 1.17 mmol), potassium carbonate (0.311 g, 2.26 mmol) and dioxan:water (4.5 mL:0.5 mL). This solution was degassed with $N_2$ for 10 min and then the Pd(dppf)Cl$_2$.DCM complex (0.110 g, 0.135 mmol) was added. The reaction was heated at 100° C. for 16 h. Upon completion, the reaction was diluted with ethylacetate and filtered through a celite bed. The filtrate was partitioned between ethylacetate and water. The ethylacetate layer was dried over $Na_2SO_4$ and concentrated under reduced pressure. The obtained crude product was purified by flash column chromatography (neutral alumina) eluting the required compound [3-(1,3-Dimethyl-1H-indazol-5-yl)-2,5-dimethyl-pyrazolo[1,5-a]pyrimidin-7-yl]-(2-methyl-pyridin-4-ylmethyl)-carbamic acid tert-butyl ester (0.2 g, 43.4%) with 30% ethylacetate-hexanes as an off-white solid.

Step 4: 3-(1,3-dimethyl-1H-indazol-5-yl)-2,5-dimethyl-N-[(2-methylpyridin-4-yl)methyl]pyrazolo[1,5-a]pyrimidin-7-amine To an ice cold solution of [3-(1,3-Dimethyl-1H-indazol-5-yl)-2,5-dimethyl-pyrazolo[1,5-a]pyrimidin-7-yl]-(2-methyl-pyridin-4-ylmethyl)-carbamic acid tert-butyl ester (0.2 g, 0.388 mmol) in dichloromethane (2 mL) was added trifluoroacetic acid (TFA) (2 mL) dropwise. After completion of addition, the reaction mass was stirred at ambient temperature for 6 h. After completion of the reaction, the solvent and excess TFA were distilled out. The crude product was basified with 1N NaOH solution and extracted with 10% MeOH-DCM. The organic layers were dried over $Na_2SO_4$ and concentrated. The obtained crude product was purified by flash column chromatography (neutral alumina) eluting the required compound Ex. 4 (0.06 g, 37.7%) with 70% ethylacetate-hexanes as an off-white solid.

Examples 5-8 were synthesized using the same general methods as described for Examples 3 and 4.

Example 5

3-(1,3-dimethyl-1H-indazol-5-yl)-2,5-dimethyl-N-[(2-ethylpyridin-4-yl)methyl]pyrazolo[1,5-a]pyrimidin-7-amine

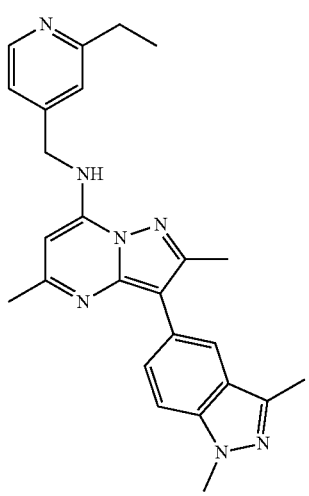

Example 6

3-(1,3-dimethyl-1H-indazol-5-yl)-2,5-dimethyl-N-[(2-methoxypyridin-4-yl)methyl]pyrazolo[1,5-a]pyrimidin-7-amine Example 7

3-(1,3-dimethyl-1H-indazol-5-yl)-2,5-dimethyl-N-[(2-cyanopyridin-4-yl)methyl]pyrazolo[1,5-a]pyrimidin-7-amine

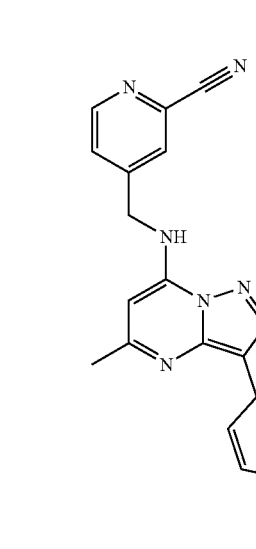

Example 8

3-(1,3-dimethyl-1H-indazol-5-yl)-2,5-dimethyl-N-[(2-trifluoromethylpyridin-4-yl)methyl]pyrazolo[1,5-a]pyrimidin-7-amine

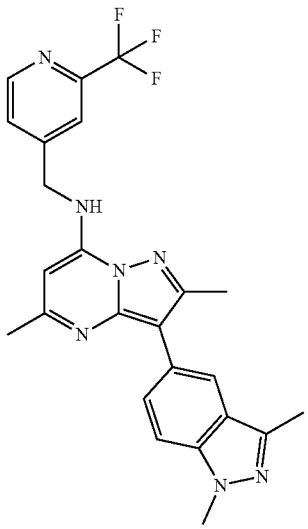

Analytical data for the compounds of Examples 1-8 are shown in Table 1.

TABLE 1

| Ex. No. | Analytical Data |
|---|---|
| 1 | $^1$H-NMR (DMSO-d6, 300 MHz): δ 8.36 (d, 1 H), 7.95 (s, 1 H), 7.28 (d, 1 H), 7.16 (m, 3 H), 7.07 (d, 1H), 5.82 (s, 1 H), 4.15 (s, 2 H), 3.78 (d, 6 H), 2.43 (s, 3 H), 2.23 (s, 3 H), LCMS: 404.3 [M + H], HPLC purity: 99.9% |
| 2 | $^1$H-NMR (DMSO-d6, 300 MHz): δ 8.18 (d, 1 H), 8.02 (s, 1 H), 7.33 (d, 1H), 7.28 (d, 1 H), 7.16 (dd, 1 H), 7.1 (d, 1H), 7.07 (d, 1H), 5.91 (s, 1 H), 4.61 (s 2 H), 3.80 (d, 6 H), 2.43 (s, 3 H), 2.24 (s, 3 H), LCMS: 408.5 [M + H], HPLC purity: 99.5% |
| 3 | $^1$H-NMR (CDCl$_3$, 300 MHz): δ 8.25 (d, 1 H), 7.88 (s, 1 H), 7.75 (dd, 1H), 7.42 (d, 1 H), 7.22 (d, 1 H), 6.97 (s, 1H), 6.76 (dd, 1H), 5.68 (s, 1 H), 4.70 (s, 2 H), 4.03 (d, 3 H), 2.61 (s, 6 H), 2.47 (s, 3 H), LCMS: 416.4 [M + H], HPLC purity: 99.7% |
| 4 | $^1$H-NMR (CDCl$_3$, 300 MHz): δ 8.52 (d, 1 H), 7.88 (s, 1 H), 7.75 (dd, 1H), 7.41 (d, 1 H), 7.21 (d, 1 H), 7.17 (d, 1H), 6.73 (m, 1H), 5.69 (s, 1 H), 4.64 (s, 2 H), 4.03 (d, 3 H), 2.61 (s, 9 H), 2.47 (s, 3 H), LCMS: 412.3 [M + H], HPLC purity: 99.6% |
| 5 | $^1$H-NMR (CDCl$_3$, 300 MHz): δ 8.52 (d, 1 H), 7.88 (s, 1 H), 7.75 (dd, 1H), 7.42 (d, 1 H), 7.18 (s, 1 H), 7.14 (d, 1H), 6.69 (m, 1H), 5.71 (s, 1 H), 4.63 (s, 2 H), 4.03 (d, 3 H), 2.85 (q, 2 H), 2.61 (s, 6 H), 2.47 (s, 3 H), 1.32 (t, 3 H), LCMS: 426.4 [M + H], HPLC purity: 99.7% |
| 6 | $^1$H-NMR (CDCl$_3$, 300 MHz): δ 8.18 (d, 1 H), 7.88 (s, 1 H), 7.75 (dd, 1H), 7.41 (d, 1 H), 6.89 (d, 1H), 6.73 (m, 2H), 5.72 (s, 1 H), 4.60 (s, 2 H), 4.03 (d, 3 H), 3.95 (s, 3 H), 2.60 (s, 6 H), 2.48 (s, 3 H), LCMS: 428.4 [M + H], HPLC purity: 99.5% |
| 7 | $^1$H-NMR (CDCl$_3$, 300 MHz): δ 8.59 (d, 1 H), 8.25 (s, 1 H), 7.81 (m, 2H), 7.72 (d, 1 H), 7.49 (d, 1H), 7.41 (d, 1H), 5.68 (s, 1 H), 4.75 (d, 2 H), 4.03 (d, 3 H), 2.60 (s, 6 H), 2.48 (s, 3 H), LCMS: 441.5 [M + 18], HPLC purity: 93.7% |
| 8 | $^1$H-NMR (CDCl$_3$, 300 MHz): δ 8.76 (d, 1 H), 7.88 (s, 1 H), 7.75 (m, 2H), 7.53 (d, 1 H), 7.42 (d, 1H), 6.80 (s, 1H), 5.68 (s, 1 H), 4.75 (d, 2 H), 4.03 (d, 3 H), 2.60 (s, 6 H), 2.48 (s, 3 H), LCMS: 466.4 [M + 18], HPLC purity: 99.35% |

Example 9

Liposomal Formulation 50 mg of 3-(1,3-dimethyl-1H-indazol-5-yl)-2,5-dimethyl-N-[(2-fluoropyridin-4-yl)methyl]pyrazolo[1,5-a]pyrimidin-7-amine (Example 3) and 500 mg of soybean lecithin were transferred to a beaker. Chloroform (about 10 ml) was added and the mixture was kept under stirring until the components had dissolved completely. Then the solvent was removed by rotary evaporator to yield in a thin lipid film. Water (10 ml) was added to the lipid film and the film was allowed to rehydrate at room temperature. The formulation was mixed thoroughly and sonicated to form a fine dispersion. The formulation had a pH of 6.42.

Biological Assays

In Vitro Assay in Mammalian Cell Culture

The antiviral activity of compounds of the invention has been evaluated based on the ability of the compounds to prevent virus from causing viral cytopathic effects (CPE) in mammalian cell culture. Incubation time, cell line, cell density and virus titer differed from assay to assay but the general procedure was as follows: Cells were cultivated on 96 well flat bottom plates to approximately 90% confluence (20 000-90 000 cells/well) in a suitable medium. The titer of the virus was determined by the standard method of tissue culture infective dose (TCID$_{50}$) on cells. Briefly, cells were infected with 50 μl of virus suspension, and diluted 10-fold in medium. The plates were incubated at 37° C. with 5% CO$_2$ for 3-7 days and cells were inspected daily for CPE. After determining CPE, plates were stained with Gram's Crystal Violet solution and optical density was read at 540 nm. The highest virus dilution that resulted in >95% CPE was used in the assays. Substances at a final concentration of 2.5-20 μM and the virus were added to the cells and incubated for 3-7 days depending on the virus and cell line used. As controls, uninfected cells and cells infected with virus (no substance) were included on each plate. The cells were stained with crystal violet after determining the CPE on infected controls and the optical density was read at 540 nm. The inhibition capacity was calculated as a % by comparison with non-infected and infected controls.

The inventive compounds of Examples 1-4 were tested using the above described protocol. In addition, the same test was performed using compounds lacking a substituent in 2-position on the pyridine ring, viz. 3-(3,4-dimethoxyphenyl)-2,5-dimethyl-N-(pyridin-4-ylmethyl)pyrazolo[1,5-a]pyrimidin-7-amine (Compound "X") and 3-(1,3-dimethyl-1H-indazol-5-yl)-2,5-dimethyl-N-[(pyridin-4-yl)methyl]pyrazolo[1,5-a]pyrimidin-7-amine (Compound "Y"):

Compound X

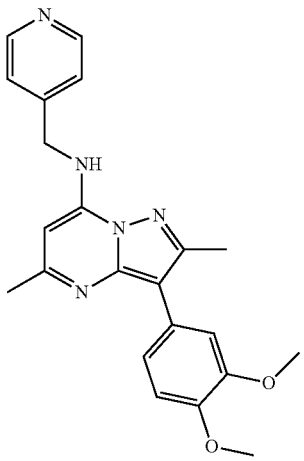

Compound Y

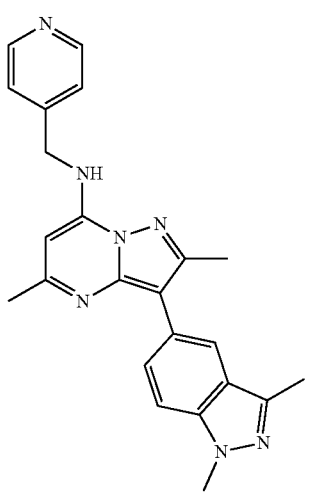

Tables 2 and 3 show the inhibition capacity of the tested compounds on different picornaviruses at 10 nM and 100 nM, respectively. EV6: enterovirus strain 6; EV30: enterovirus strain 30; EV-D68: enterovirus D68; EV71: enterovirus strain 71; Cox B1: coxsackie B virus strain 1; Cox B2: coxsackie B virus strain 2; Cox B3: coxsackie B virus strain 3; Cox B5: coxsackie B virus strain 5; Polio 1: polio virus strain 1.

TABLE 2

| Inh. at 10 nM | Comp. X | Ex. 1 | Ex. 2 | Comp. Y | Ex. 3 | Ex. 4 |
|---|---|---|---|---|---|---|
| EV6 | 100 | 100 | 100 | 100 | 88 | 100 |
| EV30 | 100 | 100 | 100 | 100 | 100 | 100 |
| EV-D68 | 86 | 85 | 73 | 85 | 76 | 81 |
| EV71 | 82 | 68 | 76 | 87 | 82 | 76 |
| Cox B1 | 100 | 93 | 100 | 100 | 68 | 100 |
| Cox B2 | 100 | 100 | 100 | 100 | 100 | 100 |
| Cox B3 | 100 | 100 | 100 | 100 | 100 | 100 |
| Cox B5 | 100 | 80 | 84 | 85 | 48 | 74 |
| Polio 1 | 100 | 100 | 100 | 100 | 100 | 100 |

TABLE 3

| Inh. at 100 nM | Comp. X | Ex. 1 | Ex. 2 | Comp. Y | Ex. 3 | Ex. 4 |
|---|---|---|---|---|---|---|
| EV6 | 100 | 100 | 100 | 100 | 100 | 100 |
| EV30 | 100 | 100 | 100 | 100 | 100 | 100 |
| EV-D68 | 86 | 83 | 68 | 80 | 70 | 70 |
| EV71 | 82 | 77 | 75 | 86 | 81 | 79 |
| Cox B1 | 100 | 100 | 100 | 100 | 100 | 100 |
| Cox B2 | 100 | 100 | 100 | 100 | 100 | 100 |
| Cox B3 | 100 | 100 | 100 | 100 | 100 | 100 |
| Cox B5 | 100 | 100 | 100 | 100 | 100 | 100 |
| Polio 1 | 100 | 100 | 100 | 100 | 100 | 100 |

In Vitro CYP 3A4 Enzyme Inhibition Study in Human Liver Microsomes by Probe Substrate Method In vitro CYP3A4 enzyme inhibition assay was performed using Human liver microsomes at 0.5 mg/mL concentration. Ketoconazole was used as reference inhibitor and Midazolam was used as selective probe substrate for CYP 3A4 enzyme. Serial dilution of test/control items was prepared in potassium phosphate buffer (50 mM, pH 7.40) to obtain eight concentrations each in a 1:4 dilution pattern. The percentage of acetonitrile/DMSO was maintained at 2.5%/0.25% in 2.5× serially diluted control/test item solutions respectively. The final percentage of acetonitrile/DMSO was 1%/0.1% respectively. Intermediate solutions such as 10× working solution (5 mg/mL) of Human liver microsomal solution, 10× concentration of reference probe substrates in buffer, 5× concentrations of Cofactors (5.0 mM NADP+, 25.0 mM G-6-P, 3.0 IU/mL G-6-PDH and 10.0 mM $MgCl_2$) were prepared in potassium phosphate buffer. The final concentration of liver microsomes in the reaction mixture was 0.5 mg/mL, cofactors was 1.0 mM NADP+, 5.0 mM G-6-P, 0.6 IU/mL G-6-PDH and 2.0 mM $MgCl_2$. Midazolam was tested at 5 μM test concentration. 40 μL of 2.5× serially diluted test/control item solutions and 10 μL of 5× liver microsomal solution were added to 96 well plate and incubated for 10 min at 37° C. with shaking condition (400 rpm) using Thermomixer. After pre incubation, 20 μL of potassium phosphate buffer, 10 μL of respective probe substrate working solution and 20 μL of cofactor mix was added. The results, expressed as $IC_{50}$ in μM, are shown in Table 4.

TABLE 4

| Compound | Comp. X | Ex. 1 | Ex. 2 | Comp. Y | Ex. 3 | Ex. 4 |
|---|---|---|---|---|---|---|
| $IC_{50}$ μM | 0.97 | 23.1 | >25 | 0.28 | >25 | >25 |

Pharmacokinetics Properties
Formulation Preparation 10 mg of the compound was weighed and transferred to graduated tube. Then 500 μL of DMA (5% v/v) was added, vortex mixed thoroughly and sonicated till test item was completely dissolved. Then 5 mL of PEG 200 (50% v/v) were added, and vortex mixed thoroughly. Thereafter, Sterile Water for Injection (SWFI) was added in small increments and vortex mixed thoroughly. Finally, the volume was made up to 10 mL with SWFI (45% v/v) to obtain a clear solution with final formulation strength of 1 mg/mL. The pH of the formulation was found to be 6.51. Formulation was freshly prepared before the administration to animals.

Dose Administration

Adult healthy male Sprague Dawley rats aged 8-10 weeks were used for experimentation after a minimum 3 days of acclimation. Fasted animals were administered with test compound in recommended vehicle (5% DMA+50% PEG 200+45% SWFI) by oral route at a dose of 10 mg/kg body weight and at dose volume of 10 mL/kg body weight.

Under mild isoflurane anesthesia, blood specimens were collected into pre-labeled tubes containing anticoagulant ($K_2$EDTA—2 mg/mL blood) at different time points post dose. Collected blood specimens were centrifuged at 4000 rpm, 4° C. for 10 minutes and plasma were separated and stored at −80° C. until analysis. The results are shown in Table 5.

TABLE 5

|  | Comp. Y | Ex. 4 | Ex. 3* |
|---|---|---|---|
| Dose (mg/kg bw,) | 10 | 10 | 50 |
| $C_{max}$ (mg/mL) | 2.3 ± 0.3 | 2.5 ± 0.9 | 2.3 ± 0.8 |
| $T_{max}$ (h) | 1.2 ± 0.8 | 1.3 ± 0.6 | 6 ± 2 |
| $AUC_{last}$ (h*mg/mL) | 14.8 ± 2.6 | 25.2 ± 10.0 | 42.4 ± 11.7 |
| $AUC_{inf}$ (h*mg/mL) | 15.5 ± 1.9 | 27.4 ± 10.1 | 129.8 ± 55.8 |
| $AUC_{extrap}$ (%) | 4.6 ± 5.6 | 8.5 ± 5.2 | 64..5 ± 13.5 |
| $T_{1/2}$ (h) | 3.4 ± 1.2 | 6.8 ± 1.5 | 41.5 ± 19.7 |
| $MRT_{last}$ (h) | 4.4 ± 1.1 | 6.7 ± 0.6 | 11.3 ± 0.5 |

*Liposomal formulation

Metabolic Stability

Metabolic stability assay was carried out using Human/Rat liver microsomes. The final composition of the assay included 5 μM of test items and Control items (Diclofenac or Imipramine) prepared from DMSO stock, so that the final concentration of DMSO was 0.1%, 0.25 mg/mL microsomal protein and cofactors (5.0 mM G-6-P, 0.06 U/mL G-6-PDH, 2.0 mM $MgCl_2$, 1.0 mM NADP+). Test item/Control items were incubated with Human/Rat liver microsomes with cofactors and without cofactors. The reaction mixture (100 μL) was removed at specified time period and the reaction was stopped by addition of stop solution. The samples were extracted in presence of internal standard and were analyzed using LC-MS/MS. The percent of the test/Control item remaining after specified incubation period was calculated with respect to the peak area ratio at time 0 min.

Brief Protocol

4× working concentration of test item (20 μM)/Control items (20 μM) were prepared in 50 mM Potassium phosphate buffer (pH 7.4) using 5 mM DMSO stocks. 10× working concentration of Human/Rat liver microsomal solution (2.5 mg/mL) was prepared in 50 mM Potassium phosphate buffer (pH 7.40) using stock solution of Human/Rat liver microsomes (20 mg/mL protein concentration). The reaction mixture of 100 μL (for each time point) was incubated by adding 45 μL potassium phosphate buffer, 10 μL of diluted Human/Rat liver microsomal solution (2.5 mg/mL), 25 μL of test/Control items (20 μM) and 20 μL of Cofactors/Buffer. The reaction mixture was incubated further at 37° C. for specified incubation time points (With Cofactors: 0, 15, 30, 60 and 120 min; Without Cofactors: 0 and 120 min). 100 μL incubation samples of test items and Control items at specified incubation time points were transferred to respective tubes for sample extraction.

Protein Precipitation Extraction Method

Test and Control item specimens were extracted by Protein precipitation method. A 100 μL incubation sample at each time point was added to tubes containing 200 μL of ice-cold acetonitrile and 50 μL Haloperidol solution (0.5 μg/mL). Then the tubes were vortex mixed thoroughly and centrifuged at 10000 rpm for 10 minutes at 4° C. A clear supernatant of 200 μL of samples were submitted for LC-MS/MS analysis. The results, expressed as % remaining after incubation for 60 min, are shown in Table 6.

TABLE 6

| Compound | Human microsomes | Rat microsomes |
|---|---|---|
| Comp. Y | 86.2% | 89.7% |
| Ex. 3 | 96.1% | 99.4% |
| Ex. 4 | 90.0% | 84.0% |

Human and Rat Plasma Protein Binding

Methodology

Plasma protein binding study was performed using a Rapid Equilibrium Dialysis (RED) device containing dialysis membrane with a molecular weight cut-off of 8,000 Daltons. Each dialysis insert contained two chambers. The red chamber was for the plasma while the white chamber was for the buffer. Test items and Control items (Warfarin and Propranolol) were prepared at a required test concentration of 10 μM in Human/Rat plasma (pH adjusted to 7.40) using 10 mM DMSO stocks (final DMSO concentration was 0.1%). 300 μL of plasma sample was added into the sample chamber. 500 μL of buffer was added into the buffer chamber. After sealing the RED device with an adhesive film, incubation was done at 37° C. with shaking at 300 rpm for 4 h. Following incubation, an aliquot of 50 μL was removed from each well (plasma and buffer side) and diluted with equal volume of opposite matrix to nullify the matrix effect and subjected for sample extraction.

Protein Precipitation Extraction Method

All samples were extracted by Protein Precipitation method by adding 200 μL of ice cold Acetonitrile and 50 μL of internal standard (Haloperidol at 0.1 μg/mL) solution. The tubes were vortex mixed thoroughly and centrifuged at 10000 rpm, 4° C. for 10 minutes. A clear supernatant of 200 μL of samples were submitted for LC-MS/MS analysis. The results, expressed as % plasma protein binding, are shown in Table 7.

TABLE 7

| Compound | Human plasma | Rat plasma |
|---|---|---|
| Compd. Y | 97.3% | 97.6% |
| Ex. 3 | 97.8% | 94.1% |
| Ex. 4 | 98.5% | 98.3% |

The invention claimed is:

1. A compound of formula (I)

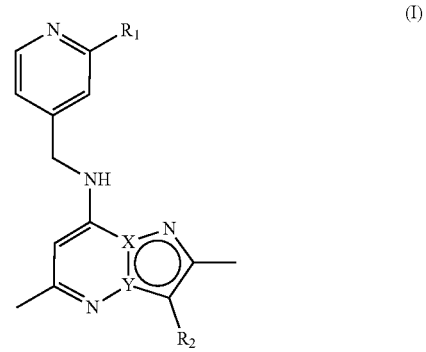

or a pharmaceutically acceptable salt thereof, wherein
one of X and Y is C and the other one is N;
$R_1$ is selected from fluoro and methyl; and
$R_2$ is 3,4-dimethoxyphenyl or 1,3-dimethyl-1H-indazol-5-yl.

2. The compound according to claim 1, or a pharmaceutically acceptable salt thereof, wherein $R_2$ is 3,4-dimethoxyphenyl.

3. The compound according to claim 1, or a pharmaceutically acceptable salt thereof, wherein $R_2$ is 1,3-dimethyl-1H-indazol-5-yl.

4. The compound according to claim 1, or a pharmaceutically acceptable salt thereof, wherein $R_1$ is fluoro.

5. The compound according to claim 1, or a pharmaceutically acceptable salt thereof, wherein $R_1$ is methyl.

6. The compound according to claim 1, wherein X is N, and Y is C.

7. The compound according to claim 1, wherein X is C, and Y is N.

8. The compound according to claim 1, wherein the compound is selected from
- 3-(3,4-dimethoxyphenyl)-2,6-dimethyl-N-((2-methylpyridin-4-yl)methyl) imidazo[1,2-b]pyridazin-8-amine,
- 3-(3,4-dimethoxyphenyl)-N-((2-fluoropyridin-4-yl)methyl)-2,6-dimethylimidazo[1,2-b]pyridazin-8-amine,
- 3-(1,3-dimethyl-1H-indazol-5-yl)-2,5-dimethyl-N-[(2-fluoropyridin-4-yl)methyl]pyrazolo[1,5-a]pyrimidin-7-amine, and
- 3-(1,3-dimethyl-1H-indazol-5-yl)-2,5-dimethyl-N-[(2-methylpyridin-4-yl)methyl]pyrazolo[1,5-a]pyrimidin-7-amine, or a pharmaceutically acceptable salt thereof.

9. A pharmaceutical composition comprising a compound according to claim 1, or a pharmaceutically acceptable salt thereof, and optionally a pharmaceutically acceptable excipient.

10. A method for the treatment of a picornaviral infection in a mammal, which comprises administering an effective amount of the compound or pharmaceutically acceptable salt according to claim 1 to the mammal.

11. The compound according to claim 2, or a pharmaceutically acceptable salt thereof, wherein $R_1$ is methyl.

12. The compound according to claim 2, wherein X is N, and Y is C.

13. The compound according to claim 2, wherein X is C, and Y is N.

14. The compound according to claim 3, or a pharmaceutically acceptable salt thereof, wherein $R_1$ is methyl.

15. The compound according to claim 3, wherein X is N, and Y is C.

* * * * *